United States Patent
Baldini et al.

(10) Patent No.: US 9,772,292 B2
(45) Date of Patent: Sep. 26, 2017

(54) FIBER OPTIC PROBE AND MEASURING SENSOR USING SAID PROBE

(75) Inventors: Francesco Baldini, Florence (IT); Cosimo Trono, San Casciano Val di Pesa (IT)

(73) Assignee: COSIGLIO NAZIONALE DELLE RICERCHE, Rome (IT)

( * ) Notice: Subject to any disclaimer, the term of this patent is extended or adjusted under 35 U.S.C. 154(b) by 715 days.

(21) Appl. No.: 13/991,011

(22) PCT Filed: Nov. 30, 2011

(86) PCT No.: PCT/IT2011/000392
§ 371 (c)(1),
(2), (4) Date: Oct. 11, 2013

(87) PCT Pub. No.: WO2012/073267
PCT Pub. Date: Jun. 7, 2012

(65) Prior Publication Data
US 2014/0051177 A1    Feb. 20, 2014

(30) Foreign Application Priority Data
Dec. 3, 2010  (IT) .................. FI2010A0237

(51) Int. Cl.
G01N 21/77    (2006.01)
A61B 5/1459   (2006.01)
G01N 21/80    (2006.01)

(52) U.S. Cl.
CPC .......... *G01N 21/77* (2013.01); *A61B 5/1459* (2013.01); *G01N 21/7703* (2013.01); *G01N 21/80* (2013.01)

(58) Field of Classification Search
CPC ..................................................... G01N 21/77

(Continued)

(56) References Cited

U.S. PATENT DOCUMENTS 4,476,870 A * 10/1984 Peterson .............. A61B 5/1459
250/458.1
4,682,895 A *  7/1987 Costello ............. G01N 21/7703
250/227.11

(Continued)

FOREIGN PATENT DOCUMENTS

EP    323816 A    7/1989
EP    0 633 465 A1  1/1995

OTHER PUBLICATIONS

F. Baldini, G. Ghini, A. Giannetti, F. Senesi, C. Trono "A novel optical probe for pH sensing in gastro-esophageal apparatus", Proc. of SPIE vol. 7890, Advanced Biomedical and Clinical Diagnostic Systems IX, 78901J, Feb. 21, 2011, pp. 78901J-1 to 78901J-6.*

*Primary Examiner* — Christine T Mui
*Assistant Examiner* — Emily Berkeley
(74) *Attorney, Agent, or Firm* — McGlew and Tuttle, P.C.

(57) ABSTRACT

The fiber optic probe (7) comprises: a first optical fiber (9) to convey an electromagnetic radiation towards a measuring area at an exit end of said first optical fiber (9); a second optical fiber (11) to collect an electromagnetic radiation from said measuring area, the second optical fiber comprising an entrance end arranged in the measuring area and adjacent to the exit end of the first optical fiber. The exit end of the first optical fiber and the entrance end of the second optical fiber (11) are treated so that at least part of the electromagnetic radiation conveyed along the first optical fiber exits laterally from the first optical fiber and enters laterally in the second optical fiber. Moreover, in the measuring area an indicating material (15) is arranged, indicating a parameter to be measured with the probe. The radiation exiting from the first optical fiber passes through the indicating material so that the radiation collected by the second optical fiber is modulated by the indicating material (15).

22 Claims, 2 Drawing Sheets

(58) Field of Classification Search
 USPC .......................................................... 436/163
 See application file for complete search history.

(56) References Cited

U.S. PATENT DOCUMENTS

| | | | | |
|---|---|---|---|---|
| 4,752,115 | A | * | 6/1988 | Murray, Jr. ............ C09K 11/06 356/41 |
| 5,530,779 | A | | 6/1996 | Baldini et al. |
| 5,953,477 | A | * | 9/1999 | Wach ................. A61B 5/14546 385/115 |
| 6,472,163 | B1 | * | 10/2002 | Coleman ................. C12Q 1/02 422/50 |
| 2005/0069243 | A1 | * | 3/2005 | Ukrainczyk ....... G01N 21/7703 385/12 |
| 2008/0146902 | A1 | * | 6/2008 | Hacker ............. A61B 5/14539 600/342 |
| 2009/0088615 | A1 | | 4/2009 | Robinson et al. |
| 2010/0022861 | A1 | * | 1/2010 | Cinbis ................. A61B 5/0084 600/325 |

* cited by examiner

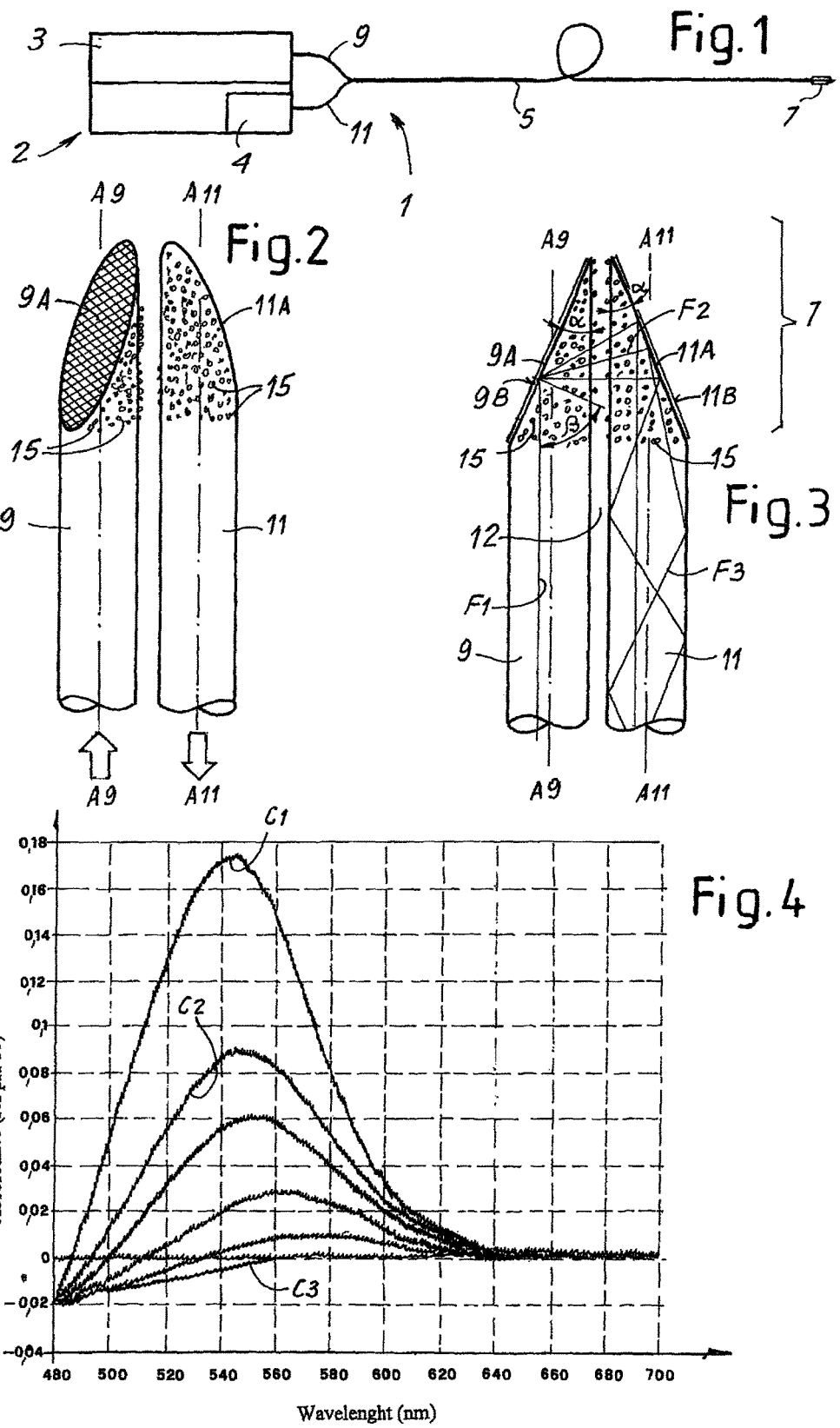

FIBER OPTIC PROBE AND MEASURING SENSOR USING SAID PROBE

TECHNICAL FIELD

The present invention relates to a fiber optic probe, in particular, but not exclusively, a fiber optic pH probe, which can be used, for example, to measure the pH in the gastro-esophageal tract or in other situations in which the use of a sensor with limited invasiveness is required.

STATE OF THE ART

EP-A-323816 describes a sensor for measuring absorption of gastric contents for medical use, in particular a probe for measuring gastro-esophageal reflux. The sensor comprises three optical fibers, two to transmit electromagnetic radiations, at two different wavelengths, and one to collect the electromagnetic radiation reflected by a mirror placed in front of the terminal ends of the three optical fibers. Between these ends and the reflecting mirror a volume is provided, into which the medium in which the sensor is immersed can flow. Modulation of the electromagnetic radiation caused by the medium interposed between the ends of the optical fibers and the mirror is used to detect a condition of gastro-esophageal reflux.

Although this probe is particularly efficient, it has non-negligible overall dimensions due to the large cross section of the sensor.

U.S. Pat. No. 5,530,779 describes a fiber optic sensor, which can be used for example as a pH sensor obtained by anchoring controlled porosity glass particles or beads to the terminal end of a plastic optical fiber. The controlled porosity glass beads are impregnated with a chromophore, i.e. a substance whose electromagnetic absorption spectrum varies when there is a variation, for example, of a chemical parameter such as the acidity of the medium in which the sensor is inserted. The electromagnetic radiation conveyed by the optical fiber is modulated by the chromophore absorbed on the controlled porosity glass beads and collected by the same fiber.

US-A-2009/0088615 discloses an indwelling fiber optic probe for blood glucose measurement. In one embodiment disclosed therein, the probe includes two optical fibers arranged in parallel and distanced from one another. Optical radiation conveyed by a first one of said optical fibers exits laterally from the optical fiber and enters through the side surface of the second optical fiber. The ends of the first and second optical fibers are cut and treated to prevent optical radiation to escape from the cut surfaces of the fibers. The two fibers are arranged at a distance one from another, defining an empty volume between the fibers. During use, blood fills in the empty volume between the fibers. The light emitted by the first optical fiber and collected by the second optical fiber is modulated by the blood which fills the space between the two fibers. In this known probe, therefore, the liquid in which the probe tip is immersed is responsible for directly modulating the optical radiation which is transmitted through the liquid located between the two optical fibers.

US-A-2008/0146902 discloses a single-fiber probe for pH measurements. A dye layer is retained in front of the tip of the single fiber and brought in contact with the liquid, the pH value whereof is to be measured. In some embodiments, the tip of the fiber is cut at an angle which allows the radiation to exit the end surface of the fiber and to re-enter the fiber after having crossed a layer of dye material. The dye material is retained between the front surface of the optical fiber and an overcoat layer.

SUMMARY OF THE INVENTION

The object of an embodiment of the present invention is to provide a fiber optic probe to measure a chemical parameter, for example the pH, of a medium in which the probe is immersed, which is efficient and can be used where limited invasiveness is required, having particularly small dimensions.

Substantially, the invention provides for a fiber optic probe comprising: a first optical fiber to convey an electromagnetic radiation towards a measuring area at an exit end of said first optical fiber; a second optical fiber to collect an electromagnetic radiation from said measuring area, an entrance end of said second optical fiber being arranged in said measuring area and arranged adjacent to the exit end of said first optical fiber, wherein:

the exit end of the first optical fiber and the entrance end of the second optical fiber are treated so that at least part of the radiation conveyed along the first optical fiber exits laterally from said first optical fiber and enters laterally in said second optical fiber;
in the measuring area an indicating material is arranged indicating a parameter to be measured with the probe;
and the radiation exiting from the first optical fiber passes through the indicating material, the radiation collected by the second optical fiber being modulated by said indicating material.

With an arrangement of this type, a probe of extremely limited dimensions is obtained, which can be easily miniaturized and is therefore particularly suitable for medical uses, for example for measurements inside the gastro-intestinal tract.

To obtain a probe of particularly limited dimensions, the first optical fiber and the second optical fiber are arranged adjacent to each other and in reciprocal contact. Reciprocal contact is intended as physical proximity of the two fibers, optionally with the interposition of indicating material between them. When the indicating material is adhering to the surface of at least one fiber, the two fibers are preferably in contact with the indicating material interposed between them and therefore reciprocal contact between the fibers is actually mediated by the presence of the indicating material in the intermediate area between the two fibers. In practice, the reciprocal distance between the optical fibers can be equal to or lower than 1000 micrometers, for example equal to or lower than 800 micrometers, preferably equal to or lower than 500 micrometers. This distance is intended as preferably measured at a surface area of the fibers devoid of interposed indicating material. In particularly advantageous embodiments, this distance is equal to or less than 100 micrometers. The diameter of each optical fiber is also limited, for example less than 1 mm (1000 micrometers) and preferably less than 800 micrometers, more preferably less than 500 micrometers, and even more preferably less than 300 micrometers.

Particularly compact probes (and therefore adapted to be miniaturized, for medical or other uses which require particularly small dimensions of probe) are obtained using a single optical fiber to convey the electromagnetic radiation and a single optical fiber to collect the electromagnetic radiation modulated by said indicating material. In some embodiments, a probe of this type can be incorporated or integrated in a more complex instrument, which has, for example, other optical fibers to perform other types of detecting or measuring operations.

In some embodiments of the invention the indicating material is anchored on the side surface of at least one of said first and said second optical fiber and preferably on the side surface or on part of the end side surface of both fibers. Anchoring can be obtained, for example, by softening a fiber made of plastic material and consequently partially embedding the indicating material, for example in the form of beads of porous glass in which a chromophore is included.

Advantageously, in preferred embodiments of the invention the ends of the two optical fibers are cut according to respective planes inclined with respect to the optical axes of the optical fibers. The cut angle is such that the perpendicular to the surface generated by the cut forms, with the axis of the fiber, an angle at least close to or greater than the angle of total reflection of the incident radiation.

Preferably, to limit the exit of electromagnetic radiation from the surface defined by the cut planes to a minimum, these surfaces are treated with a reflecting or diffusing treatment. In this way, the probe can also function if immersed in a liquid medium, which (were this treatment not be provided) would cause the electromagnetic radiation to exit from the cut surface of the end of the fiber, and consequently loss of signal.

Preferred embodiments of the probe according to the invention, with fibers having cut ends treated with a reflecting and/or diffusing coating make it possible to perform a method for measuring a parameter of a fluid medium, comprising the steps of: immersing in said fluid medium, preferably a liquid medium, the ends of at least a first optical fiber and a second optical fiber forming a probe as described above; conveying an electromagnetic radiation through said first optical fiber towards a measuring area; transmitting at least a part of said electromagnetic radiation laterally outside said first optical fiber; modulating said electromagnetic radiation transmitted outside said first optical fiber through the interaction with said indicating material; collecting through the side surface of the second optical fiber a modulated electromagnetic radiation.

Advantageously, according to some embodiments, the indicating material is included or immobilized in a controlled porosity glass.

The parameter measured can, for example, be the pH, and in this case the indicating material can be an acid-base indicator, such as methyl red.

The invention also relates to a measuring sensor comprising an electromagnetic radiation emitter, an electromagnetic radiation receiver and optical guides towards a probe as defined above.

BRIEF DESCRIPTION OF THE DRAWINGS

The invention will be better understood by following the description and accompanying drawing, which shows a practical non-limiting embodiment of the invention. More in particular, in the drawing:

FIG. 1 shows a measuring sensor or instrument using a probe according to the invention:

FIG. 2 shows a perspective view of the exit end and of the entrance end of the two fibers in the measuring area;

FIG. 3 shows a side view of the ends of the fibers arranged adjacent to each other;

FIG. 4 shows the response of the sensor to the various pH conditions as a function of the wavelength of the electromagnetic radiation used for measuring;

DETAILED DESCRIPTION OF EMBODIMENTS OF THE INVENTION

Figure 5:
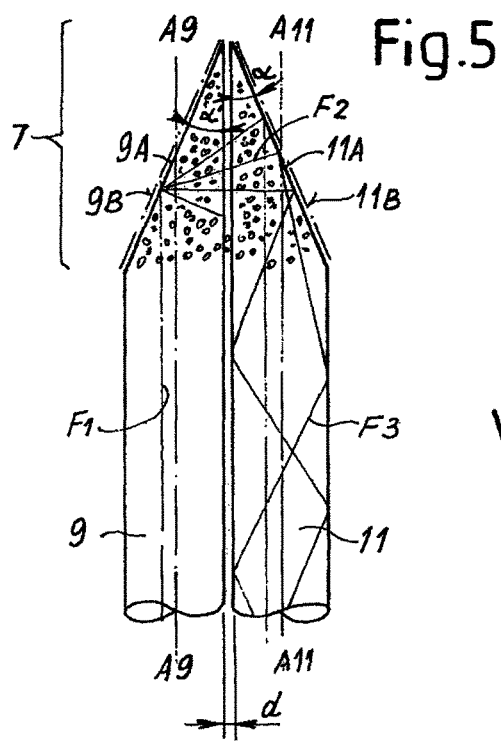
FIG. 5 shows a side view of the ends of the two fibers forming the probe in a particularly compact configuration.

FIG. 1 schematically indicates an instrument or sensor 1 for measuring a generic parameter, according to the type of probe. The teachings on which the present invention is based can be used for measuring various chemical-physical parameters, for example using suitable sensitive materials applied on the ends of the electromagnetic radiation transmission and reception fibers forming the fiber optic probe. Below, specific reference will be made to the preferred embodiment of the invention, in which the probe is designed for measuring acidity, i.e. for measuring the pH of a medium, for example a fluid (typically a liquid), in which the probe is immersed.

The sensor 1 comprises a device 2 with a light radiation source 3, for example a laser, a light emitting diode (LED) optionally with optical filter, or a wide spectrum source, and an optical detector 4, for example a photodiode. The cable, or other optical guide 5, terminating in 7 with the probe itself, is connected at the exit of the light radiation source 3. The cable, or other optical guide 5, can comprise a plurality of optical fibers and in particular a pair of optical fibers, one for transmitting and one for receiving electromagnetic radiation coming from the source 3. The probe can be produced by directly treating the optical fibers forming the cable or optical guide 5, or by interfacing with a generic pair of optical fibers forming the terminal part of the cable or optical guide 5, a terminal end constituted by a distinct optical guide, for example in turn formed of a pair of optical fibers, each of which couples to the respective two optical fibers forming the terminal part of the cable or optical guide 5.

FIGS. 2 and 3 show in greater detail the probe 7 constituted by the ends of the optical fibers forming the optical guide 5. In FIGS. 2 and 3, the optical fibers are indicated with 9 and 11. The optical fiber 9 forms an optical guide for the transmission of the electromagnetic radiation emitted by the light radiation source 3 toward the probe 7. The optical fiber 11 constitutes an optical guide for the electromagnetic radiation collected at the measuring area in which the ends of the pair of optical fibers 9, 11 forming the probe 7 are immersed.

The ends respectively of the first optical fiber and of the second optical fiber are cut according to planes inclined with respect to the axes A9 and A11 of the optical fibers 9 and 11. In this way, each optical fiber 9, 11 has a substantially flat surface, indicated respectively with 9A and 11A, whose inclination a with respect to the optical axis of the respective fiber is determined on the basis of considerations set forth below.

The cut angle is selected so as to make use of the phenomenon of total reflection of the electromagnetic radiation conveyed along the optical fiber. In general, the cut angle will be such that the straight line perpendicular to the cut plane will form, with the axis of the fiber, an angle (indicated with $\beta$) equal to or greater than the angle of total reflection, which is a function of the material with which the fibers 9 and 11 are constituted and of the medium in which these fibers are immersed. Alternatively, the angle $\beta$ can be less than the angle of total reflection and in this case the surfaces 9A and 11A are treated to prevent the electromagnetic radiation from exiting through said surfaces. In some advantageous embodiments, the faces 9A and 11A of the fibers are painted with a white diffusing material, indicated schematically with 9B and 11B in FIG. 3.

Also in the case where the angle β is equal to or greater than the angle of total reflection, the outside surface of the faces 9A, 11A of the fibers 9 and 11 is preferably painted or in any case provided with a coating that prevents destruction of the reflection in the case of immersion of the probe in a liquid medium. In fact, in the absence of painting or other surface coating, immersion of the fiber in a liquid would cause much of the radiation conveyed by the fiber to exit from the face 9A, thus compromising the measurements performed in a liquid medium.

On at least part of the remaining cylindrical surface, i.e. the part not involved by the cut that generates the flat surfaces 9A and 11A, a sensitive material, generically indicated with 15, is anchored or applied on the ends of the fibers 9, 11 (or on at least one of said fibers).

In some advantageous embodiments, said material is a pH indicating material.

In some embodiments, the sensitive material is constituted by or included in controlled porosity glass particles, beads, or powders. This glass can be anchored on the optical fibers 9 and 11 through a heat treatment process, taking these fibers, formed of plastic material, to a softening temperature using the technique described in U.S. Pat. No. 5,530,779, the content of which is incorporated in the present description. This anchoring technique ensures sufficient bonding of the controlled porosity glass beads or other particles 15 in which the indicating material is absorbed, without inhibiting penetration of the medium on which the measurement is to be performed in the pores of the glass on which the sensitive material, for example a chromophore, is anchored. This latter can be constituted in particular, for example, by methyl red, when the parameter to be measured is the pH of the medium in which the sensor 7 formed by the ends of the optical fibers 9, 11 is immersed. Methyl red is a chromophore whose absorption characteristics vary when there is a pH and wavelength variation. After establishing the incident radiation, it is then possible to find the pH value of the medium, in which the sensor 7 is immersed, on the basis of modulation of the electromagnetic radiation by the chromophore, as indicated in greater detail below.

As can be seen in FIGS. 2 and 3, the controlled porosity glass beads or other support or anchoring means of the indicating material or sensitive material are preferably applied both on the inside area 12 between the two fibers 9, 11 and outside this area, and in general on the whole cylindrical surface of both fibers corresponding to the flat faces 9A and 11A. It is also possible to apply the indicating material only on the oppositely facing portions of cylindrical surface, i.e. the portions contained in the space between the two fibers, for example between two planes tangent to the two fibers.

Anchoring of the controlled porosity glass beads or other means for immobilizing the indicating material can also take place with other systems, for example with an adhesive, especially if they are applied to glass fibers rather than fibers made of thermoplastic material.

The diagram of FIG. 3 indicates a beam of incident electromagnetic radiation F1 conveyed by the optical fiber 9 towards the measuring area constituted by the probe 7 formed by the adjacent ends of the optical fibers 9 and 11 with the sensitive material 15. This beam F1 is diffused and/or reflected internally by the surface 9A of the fiber 9. The radiation is prevented from exiting from the fiber at the surface 9A both due to the angle of incidence of the beam F1 on the surface 9A and to the presence of the layer of diffusing and/or reflecting material 9B. The light radiation is reflected and/or diffused as indicated with F2 and exits laterally from the cylindrical surface of the end of the fiber 9. The radiation F2 exiting from the fiber 9 passes through the indicating material constituted by or absorbed in the beads 15 or other support means of this same indicating material. Part of the radiation F2 penetrates inside the receiving optical fiber 11, where the electromagnetic radiation is guided (beams F3) towards the detector 4 of the device 2.

FIG. 4 shows the absorption curves of the probe 7 thus designed when measuring the pH at various wavelengths of the radiation F1, using methyl red as chromophore. More in particular, the curve indicated with C1 indicates the absorption curve at a pH value of 2.24, the curve C2 indicates absorption at a pH value of 3.72, the subsequent curves indicate absorption at gradually increasing values of pH up to the curve C3 corresponding to absorption at a pH value of 9.48. It can be observed that the maximum of all the curves is around 540-560 nanometers.

Other indicators and other wavelengths can be used to measure chemical-physical parameters different from pH.

In FIGS. 2 and 3, the optical fibers 9 and 11 are placed at a reciprocal distance so that they are not even in contact in the area in which the indicating material is applied. Preferably, however, the fibers are arranged adjacent to each other, as shown schematically in FIG. 5, with reciprocal contact in the area of application of the indicating material. When this material is absorbed on the controlled porosity glass beads, in turn anchored on the surface of the fibers or at least one of these fibers, the distance between the fibers can in this case be determined by the surface roughness caused by the presence of the glass beads anchored to the fibers. The reciprocal distance between the fibers is generally defined as the minimum distance between the generally cylindrical surfaces of the two fibers in the area not treated for anchoring of the indicating material. In FIG. 5 this distance is indicated with "d". In the case of the fibers being adjacent and in contact the distance d is, for example, in the order of a few tens of micrometers, typically 30-60 micrometers, and advantageously no greater than 100 micrometers. In any case, it is particularly advantageous for this distance not to exceed 500 micrometers.

Figure 6:
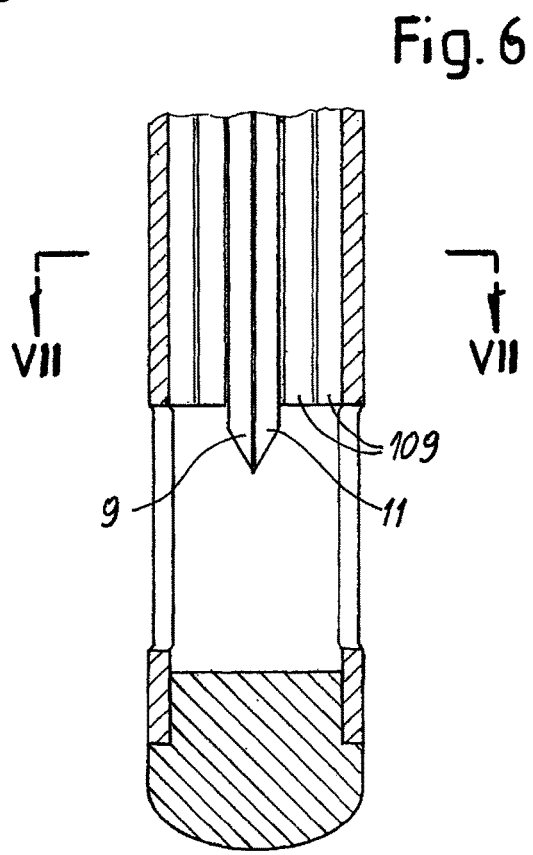
FIG. 6 shows a schematic longitudinal sectional view of a probe for multiple measurements.
Figure 7:
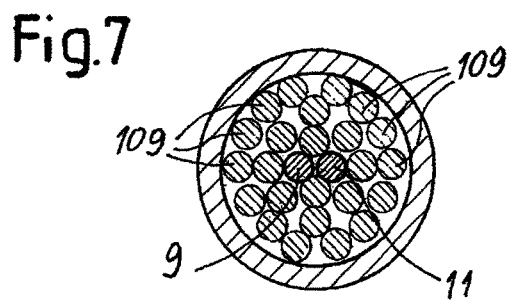
FIG. 7 shows a section according to VII-VII of FIG. 6.

FIGS. 6 and 7 schematically show the possibility of integrating the probe formed by the fibers 9 and 11 in a multiple or combined probe or sensor, i.e. provided with other optical fibers and other components to perform measurements of other types. In the specific example, the optical fibers 9, 11 forming the probe at the tip of the fibers as described above are integrated in a bundle of fibers 109 forming a probe of the type described in EP-A-323816, which describes the constructional and functional details of this device and the content of which is incorporated in the present description. This document should be referred to for further information. Therefore, in substance the probe according to the invention can be incorporated and integrated in a more complex instrument.

It is understood that the drawing merely shows an example provided purely as a practical embodiment of the invention, which may vary in forms and arrangements without however departing from the scope of the concept on which the invention is based. Any presence of reference numerals in the appended claims has the purpose of facili-

The invention claimed is:

1. A fiber optic probe comprising:
a first optical fiber to convey an electromagnetic radiation towards a measuring area at an exit end of said first optical fiber;
a second optical fiber to collect the electromagnetic radiation from said measuring area, an entrance end of said second optical fiber being arranged in said measuring area and arranged side-by-side to the exit end of said first optical fiber, said exit end of said first optical fiber and said entrance end of said second optical fiber are treated so that at least part of the electromagnetic radiation conveyed along said first optical fiber exits laterally from said at least said first optical fiber and enters laterally in said second optical fiber, at least a portion of said first optical fiber being in direct contact with at least a portion of said second optical fiber, wherein in said measuring area an indicating material is arranged indicating a parameter to be measured with said probe, and the electromagnetic radiation exiting from said first optical fiber passes through said indicating material, the electromagnetic radiation collected by said second optical fiber being modulated by said indicating material comprised in particles anchored on a side surface of at least one of said first optical fiber and said second optical fiber, said first optical fiber and said second optical fiber being arranged in contact with each other with at least part of said indicating material arranged in a contact area between said first optical fiber and said second optical fiber, said exit end of said first optical fiber comprising a first side surface and a first planar front surface, which is inclined with respect to an optical axis of said first optical fiber by an angle different than ninety degrees and said first planar front surface is adapted to prevent electromagnetic radiation from exiting through said first planar surface and further adapted to reflect or diffuse electromagnetic radiation towards said first side surface, such that said electromagnetic radiation conveyed along said first optical fiber exits laterally therefrom, said entrance end of said second optical fiber comprising a second side surface and a second planar front surface, which is inclined with respect to an optical axis of said second optical fiber by an angle different than ninety degrees and said second planar front surface is adapted to prevent electromagnetic radiation from exiting through said second planar surface and further adapted to reflect or diffuse electromagnetic radiation entering from said second side surface towards said optical axis of said second optical fiber such that said electromagnetic radiation entering said second side surface is collected by said second optical fiber.

2. A probe as claimed in claim 1, wherein said first optical fiber and said second optical fiber are arranged adjacent to each other and in reciprocal contact.

3. A probe as claimed in claim 1, wherein said first optical fiber and said second optical fiber are arranged adjacent to each other at a reciprocal distance no greater than 1000 micrometers, said distance being measured at a portion of a side surface of said first optical fiber and said second optical fiber devoid of said indicator.

4. A probe as claimed in claim 1, further comprising one single optical fiber to convey the electromagnetic radiation and one single optical fiber to collect the electromagnetic radiation modulated by said indicating material.

5. A probe as claimed in claim 1, wherein said particles are anchored on both said first optical fiber and said second optical fiber.

6. A probe as claimed in claim 1, wherein a perpendicular to each cut plane forms, with the optical axis of a respective optical fiber, an angle greater than an angle of total reflection.

7. A probe as claimed in claim 1, wherein said first planar front surface and said second planar front surface are treated with a reflecting or diffusing treatment.

8. A probe as claimed in claim 1, wherein said indicating material is a pH indicator.

9. A probe as claimed in claim 1, wherein said particles are a controlled porosity glass.

10. A probe as claimed in claim 1, wherein said indicating material is a chromophore.

11. A probe as claimed in claim 1, wherein said first optical fiber and said second optical fiber are inserted in a fiber bundle forming part of a multi-functional sensor.

12. A probe as claimed in claim 1, wherein said first optical fiber and said second optical fiber have a diameter no greater than 1000 micrometers.

13. A sensor comprising an electromagnetic radiation emitter, an electromagnetic radiation receiver and optical guides towards a probe, said probe comprising a first optical fiber to convey an electromagnetic radiation towards a measuring area at an exit end of said first optical fiber, said probe further comprising a second optical fiber to collect the electromagnetic radiation from said measuring area, an entrance end of said second optical fiber being arranged in said measuring area and arranged side-by-side to the exit end of said first optical fiber, said exit end of said first optical fiber and said entrance end of said second optical fiber being treated so that at least part of the electromagnetic radiation conveyed along said first optical fiber exits laterally from said first optical fiber and enters laterally in said second optical fiber, wherein in said measuring area an indicating material is arranged indicating a parameter to be measured with said probe, and the electromagnetic radiation exiting from said first optical fiber passes through said indicating material, the electromagnetic radiation collected by said second optical fiber being modulated by said indicating material comprised in particles anchored on a side surface of at least one of said first optical fiber and said second optical fiber, said first optical fiber and said second optical fiber being arranged in contact with each other with at least part of said indicating material arranged in a contact area between said first optical fiber and said second optical fiber, said exit end of said first optical fiber comprising a first side surface and a first planar front surface, which is inclined with respect to a first optical fiber axis of said first optical fiber by an angle different than ninety degrees and said first planar front surface is adapted to prevent electromagnetic radiation from exiting through said first planar surface and further adapted to reflect or diffuse electromagnetic radiation towards said first side surface, such that said electromagnetic radiation conveyed along said first optical fiber exits laterally therefrom, said entrance end of said second optical fiber comprising a second side surface and a second planar front surface, which is inclined with respect to a second optical fiber axis of said second optical fiber by an angle different than ninety degrees and said second planar front surface is adapted to prevent electromagnetic radiation from exiting through said second planar surface and further adapted to reflect or diffuse electromagnetic radiation entering from said second side surface towards said second optical fiber axis, such that said electromagnetic radiation entering said second side surface is collected by said second optical fiber.

14. A sensor as claimed in claim 13, wherein said electromagnetic radiation emitter is a light radiation source.

15. A sensor as claimed in claim 14, wherein said light radiation source emits a radiation comprised between 550 and 570 nm.

16. A sensor as claimed in claim 14, wherein said light radiation source comprises one of a laser, a light emitting diode (LED) and a light emitting diode (LED) associated with an optical filter.

17. A sensor as claimed in claim 13, further comprising at least one further probe for detecting a parameter different than a parameter measured by the probe formed by said first optical fiber and said second optical fiber.

18. A probe as claimed in claim 1, wherein said first optical fiber and said second optical fiber have a diameter no greater than 600 micrometers.

19. A probe as claimed in claim 1, wherein said first optical fiber and said second optical fiber have a diameter no greater than 300 micrometers.

20. A probe as claimed in claim 1, wherein said indicating material is methyl red.

21. A fiber optic probe comprising:
a first optical fiber to convey an electromagnetic radiation towards a measuring area, said first optical fiber having a first side surface and a first planar reflective surface, said first planar reflective surface being configured to reflect electromagnetic radiation conveyed along said first optical fiber toward said first side surface, said first side surface being configured to cause said electromagnetic radiation to exit therethrough towards said measuring area;
a second optical fiber to collect said electromagnetic radiation from said measuring area, said second optical fiber having a second side surface and a second planar reflective surface, said second side surface being configured to cause said electromagnetic radiation to enter therethrough from said measuring area into said second optical fiber, and said second planar reflective surface being configured to reflect electromagnetic radiation entering through said second side surface towards an axis of said second optical fiber, wherein particles of controlled porosity glass are anchored on at least one of said first side surface and said second side surface, wherein an indicating material is included in said controlled porosity glass, such that said electromagnetic radiation exiting said first side surface and entering said second side surface passes through said indicating material, and said electromagnetic radiation collected by said second optical fiber is modulated by said indicating material, said first optical fiber and said second optical fiber being arranged adjacent to one another with said controlled porosity glass particles arranged between said first optical fiber and said second optical fiber.

22. A probe as claimed in claim 1, wherein said indicating material comprises a chromophore having a characteristic of absorbing electromagnetic radiation, said characteristic varying as a function of said parameter to be detected by said probe.

* * * * *